US011333779B2

(12) United States Patent
Almeida de Carvalho et al.

(10) Patent No.: US 11,333,779 B2
(45) Date of Patent: May 17, 2022

(54) DETECTING SUBSEA HYDROCARBON SEEPAGE

(71) Applicant: Saudi Arabian Oil Company, Dhahran (SA)

(72) Inventors: Julio Alexandre Almeida de Carvalho, Dhahran (SA); Joao V. Keller, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 75 days.

(21) Appl. No.: 16/912,268

(22) Filed: Jun. 25, 2020

(65) Prior Publication Data

US 2021/0405235 A1    Dec. 30, 2021

(51) Int. Cl.
*G01V 1/30* (2006.01)
*G01N 1/08* (2006.01)
*G01N 33/24* (2006.01)

(52) U.S. Cl.
CPC ............ *G01V 1/302* (2013.01); *G01N 1/08* (2013.01); *G01N 33/24* (2013.01); *G01V 2210/641* (2013.01); *G01V 2210/643* (2013.01); *G01V 2210/644* (2013.01)

(58) Field of Classification Search
CPC ..... G01V 1/302; G01V 2210/641–647; G01N 33/24
See application file for complete search history.

(56) References Cited

U.S. PATENT DOCUMENTS

| 5,563,513 | A | * | 10/1996 | Tasci | G01V 3/02 324/359 |
| 5,724,309 | A | * | 3/1998 | Higgs | G01V 1/32 367/48 |
| 5,987,388 | A | * | 11/1999 | Crawford | G01V 1/30 367/70 |
| 6,278,949 | B1 | * | 8/2001 | Alam | G01V 1/288 702/16 |
| 6,735,526 | B1 | * | 5/2004 | Meldahl | G01V 1/28 702/14 |

(Continued)

OTHER PUBLICATIONS

Monier et al. Delineation of reservoir channels by different seismic attributes and geobody extractions for robust volumetric estimation, Saffron Field, offshore Nile Delta, Egypt, The Leading Edge (Year: 2021).*

(Continued)

*Primary Examiner* — John Fitzgerald
(74) *Attorney, Agent, or Firm* — Fish & Richardson P.C.

(57) ABSTRACT

Systems and methods for geochemical sampling grid locations on a seafloor. At least one of the methods includes generating, using received seismic data, an image representing an interpretation of a seafloor horizon surface; extracting, from the image and based on the seismic data, one or more discontinuity attributes of the seafloor horizon surface; extracting, from the image and based on the seismic data, one or more amplitude attributes of a window extending below the seafloor horizon surface; combining the one or more discontinuity attributes and the one or more amplitude attributes; and selecting, using the image and based at least partly on the combining, one or more locations of the seafloor horizon surface for sampling.

23 Claims, 10 Drawing Sheets
(7 of 10 Drawing Sheet(s) Filed in Color)

(56) References Cited

U.S. PATENT DOCUMENTS

| | | | | |
|---|---|---|---|---|
| 8,213,261 | B2* | 7/2012 | Imhof | G01V 1/32 367/38 |
| 8,483,965 | B2* | 7/2013 | Bradley | G01V 11/00 702/13 |
| 9,046,625 | B2* | 6/2015 | Sheffield | G01V 1/307 |
| 9,869,783 | B2* | 1/2018 | Jin | G01V 1/303 |
| 9,977,996 | B2* | 5/2018 | Yamada | G06K 9/209 |
| 10,067,252 | B2 | 9/2018 | Madof | |
| 10,067,253 | B2* | 9/2018 | Lowell | G01V 1/345 |
| 2003/0200030 | A1* | 10/2003 | Meldahl | G01V 1/28 702/14 |
| 2011/0002194 | A1* | 1/2011 | Imhof | G01V 1/32 367/53 |
| 2011/0118985 | A1* | 5/2011 | Aarre | G01V 1/301 702/16 |
| 2012/0038642 | A1* | 2/2012 | Wei | G01V 1/34 345/424 |
| 2013/0083626 | A1* | 4/2013 | Sheffield | G01V 1/307 367/73 |
| 2015/0047903 | A1* | 2/2015 | Gramstad | G01V 1/345 175/50 |
| 2016/0155021 | A1* | 6/2016 | Yamada | G01V 1/50 382/109 |
| 2016/0299243 | A1* | 10/2016 | Jin | G01V 1/38 |
| 2017/0068011 | A1 | 3/2017 | Hornbostel et al. | |
| 2018/0003691 | A1 | 1/2018 | N'Guessan et al. | |
| 2018/0003839 | A1* | 1/2018 | Lowell | G01V 1/345 |
| 2018/0024262 | A1* | 1/2018 | Madof | G01V 99/00 175/50 |

OTHER PUBLICATIONS

Nagakubo et al. "Fusion of 3D seismic exploration and seafloor geochemical survey for methane hydrate exploration," Exploration Geophysics (Year: 2007).* boem.gov [online], "Seismic Water Bottom Anomalies Map Gallery," available on or before Jul. 20, 2014, via Internet Archive: Wayback Machine URL <https://web.archive.org/web/20140720115329/https://www.boem.gov/Seismic-Water-Bottom-Anomalies-Map-Gallery>, retrieved on Sep. 17, 2020, URL<https://www.boem.gov/Seismic-Water-Bottom-Anomalies-Map-Gallery>.

Crutchley et al., "Seismic imaging of gas conduits beneath seafloor seep sites in a shallow marine gas hydrate province, Hikurangi Margin, New Zealand," Marine Geology, Nov. 2008, 53 pages.

Dembicki et al., "Identification, Characterization, and Ground-Truthing of Deepwater Thermogenic Hydrocarbon Macro-Seepage Utilizing High-Resolution AUV Geophysical Data," presented at the Offshore Technology Conference, Houston, Texas, Apr. 30-May 3, 2007, 10 pages.

Escalona et al., "The Challenges For Production Installations Offshore Brazil in a Complex Seafloor: How The Data From Marine Survey & Metocean Campaign Can Be Developed to Provide Better Information," presented at the Offshore Technology Conference, Houston, Texas, USA, May 4-7, 2015, 7 pages.

Jatiault et al., "Geophysical characterization of active thermogenic oil seeps in the salt province of the lower Congo basin part I: Detailed study of one oil-seeping site," Marine and Petroleum Geology, 2019, 103:753-772.

Pacal et al., "Seismic Imaging with Ocean-Bottom Nodes (OBN): Mirror Migration Technique," Conference Paper, Aug. 2015, 5 pages.

Rensbergen et al., "Fluid migration and fluid seepage in the Connemara Field, Porcupine Basin interpreted from industrial 3D seismic and well data combined with high resolution site survey data," International Journal of Earth Sciences, Feb. 2007, 96:185-197.

Roberts et al., "Seafloor reflectivity—An important seismic property for interpreting fluid/gas expulsion geology and the presence of gas hydrate," The Leading Edge, May 2006, pp. 620-628.

Schrynemeeckers, "Improving Petroleum System Identification in an Offshore Salt Environment: Gulf of Mexico and Red Sea Case Studies," Search and Discovery, Apr. 2015, Article #41607, 46 pages.

Wood et al., "Gas and gas hydrate distribution around seafloor seeps in Mississippi Canyon, Northern Gulf of Mexico, using multi-resolution seismic imagery," Marine and Petroleum Geology, 2008, 25:952-959.

Chopra et al., "Seismic attributes for stratigraphic feature characterization." SEG Technical Program Expanded Abstracts 2008. Society of Exploration Geophysicists, Jan. 2008, 1590-1594, 5 pages.

McConnell et al., "Seep-hunting in deepwater for frontier basin prospectivity assessment." World oil 229.4, Apr. 2008, 10 pages.

Nagakubo et al., "Fusion on 3D seismic exploration and seafloor geochemical survey." Proceedings of the 8th SEGJ International Symposium. Society of Exploration Geophysicists of Japan, Jan. 2006, 6 pages.

PCT International Search Report and Written Opinion in International Appln. No. PCT/US2021/038944, dated Oct. 7, 2021, 16 pages.

* cited by examiner

DETECTING SUBSEA HYDROCARBON SEEPAGE

TECHNICAL FIELD

The present disclosure generally relates to hydrocarbon exploration, including systems and methods for detecting subsea hydrocarbon seepage.

BACKGROUND

In geology, sedimentary facies are bodies of sediment that are recognizably distinct from adjacent sediments that resulted from different depositional environments. Generally, geologists distinguish facies by aspects of the rock or sediment being studied. Seismic facies are groups of seismic reflections whose parameters (such as amplitude, continuity, reflection geometry, and frequency) differ from those of adjacent groups. Seismic facies analysis, a subdivision of seismic stratigraphy, plays an important role in hydrocarbon exploration and is one key step in the interpretation of seismic data for reservoir characterization. The seismic facies in a given geological area can provide useful information, particularly about the types of sedimentary deposits and the anticipated lithology.

In reflection seismology, geologists and geophysicists perform seismic surveys to map and interpret sedimentary facies and other geologic features for applications, for example, identification of potential petroleum reservoirs. Seismic surveys are conducted by using a controlled seismic source (for example, a seismic vibrator, dynamite, or airgun) to create seismic waves. The seismic source can be located at ground surface, or floating in water above a seafloor surface. Seismic body waves travel into the ground, are reflected by subsurface formations, and return to the surface where they recorded by sensors called geophones (or hydrophones). Seismic surface waves travel along the ground surface and diminish as they get further from the surface. Seismic surface waves travel more slowly than seismic body waves. The geologists and geophysicists analyze the time it takes for the seismic body waves to reflect off subsurface formations and return to the geophones (or hydrophones) to map sedimentary facies and other geologic features. Similarly, analysis of the time it takes seismic surface waves to travel from source to sensor can provide information about near surface features. This analysis can also incorporate data from sources, for example, borehole logging, gravity surveys, and magnetic surveys.

One approach to this analysis is based on tracing and correlating along continuous reflectors throughout the dataset produced by the seismic survey to produce structural maps that reflect the spatial variation in depth of certain facies. These maps can be used to identify impermeable layers and faults that can trap hydrocarbons such as oil and gas. Particular to offshore operations, seismic surveys can be used to locate and estimate the size of offshore oil and gas reserves. To carry out such offshore surveys, ships can tow multiple airgun arrays that can emit thousands of high-decibel explosive impulses to map the seafloor.

SUMMARY

Implementations of the present disclosure provide techniques for detecting subsea hydrocarbon seepage using three-dimensional (3D) seismic data to select areas for geochemical and piston core grid sampling to test for hydrocarbon seepage. In some implementations, the techniques include: (1) extraction of dips, curvature and coherence attributes on a seafloor surface interpreted from 3D seismic data to characterize structures and discontinuities at the seafloor surface; (2) extraction of root mean square (RMS) amplitude attributes and Sweetness attributes in an interval window below the seafloor horizon surface to identify possible hydrocarbon presence indicators; and (3) combining the results from both previous steps to select areas with relatively high chances of hydrocarbon seepage detection. In some implementations, these techniques include performing seismic surveys to generate the seismic data and/or performing geochemical and piston core sampling.

In an aspect, a system is provided. The system includes: a computer-readable medium comprising computer-executable instructions; and at least one processor configured to execute the computer-executable instructions. When the at least one processor executes the computer-executable instructions, the at least one processor is configured to perform operations. The operations include: generating, using received seismic data, an image representing an interpretation of a seafloor horizon surface; extracting, from the image and based on the seismic data, one or more discontinuity attributes of the seafloor horizon surface; extracting, from the image and based on the seismic data, one or more amplitude attributes of a window extending below the seafloor horizon surface; combining the one or more discontinuity attributes and the one or more amplitude attributes; and selecting, using the image and based at least partly on the combining, one or more locations of the seafloor horizon surface for sampling.

Extracting one or more discontinuity attributes can include: performing a dip extraction analysis of the seafloor horizon surface to detect one or more first discontinuity locations that indicate potential discontinuities of the seafloor horizon surface; generating a mirror seafloor surface at a predetermined distance below the seafloor horizon surface; generating a horizon probe using the seafloor horizon surface and the mirror seafloor surface; and performing a curvature attribute analysis of the seafloor horizon surface using the horizon probe to detect one or more second discontinuity locations that indicate potential discontinuities of the seafloor horizon surface.

Extracting one or more discontinuity attributes can further include performing a variance attribute analysis of the seafloor horizon surface using the horizon probe to detect one or more third discontinuity locations that indicate potential discontinuities of the seafloor horizon surface. The mirror seafloor surface can be located 300 feet below the seafloor horizon surface.

Extracting one or more amplitude attributes can include performing an root mean square (RMS) amplitude attribute analysis of the seafloor horizon surface using a seismic volume between the seafloor horizon surface and a predetermined distance below the seafloor horizon surface to detect one or more first amplitude anomaly locations that indicate one or more locations of potential amplitude anomalies of the seafloor horizon surface. Extracting one or more amplitude attributes can include performing a sweetness seismic attribute analysis using the predetermined distance to detect one or more second amplitude anomaly locations that indicate one or more locations of potential amplitude anomalies of the seafloor horizon surface.

The operations can further include extracting, using a piston corer, a geological sample at the selected one or more locations. Selecting the one or more locations can include correlating one or more potential discontinuity locations of the seafloor horizon surface identified using the one or more discontinuity attributes with one or more potential amplitude anomaly locations identified using the one or more amplitude attributes.

These and other aspects, features, and implementations can be expressed as methods, apparatus, systems, components, program products, methods of doing business, means or steps for performing a function, and in other ways, and will become apparent from the following descriptions, including the claims.

Implementations of the present disclosure can include one or more of the following advantages. Relative to conventional techniques, the percentage of positive piston core sampling results is increased. Unlike conventional techniques, areas of the seafloor with relatively high chances of positive carbon detection in piston core samples, as compared with other areas of the seafloor, can be selected before obtaining the piston core sample.

The details of one or more implementations of these systems and methods are set forth in the accompanying drawings and the description to be presented. Other features, objects, and advantages of these systems and methods will be apparent from the description and drawings, and from the claims.

DESCRIPTION OF DRAWINGS

The patent or application file contains at least one drawing executed in color. Copies of this patent or patent application publication with color drawing(s) will be provided by the Office upon request and payment of the necessary fee.

Like reference symbols in the various drawings indicate like elements.

DETAILED DESCRIPTION

New frontier exploration can be a very risky and costly exercise. One technique that can be used to minimize exploration risk and add value in the early phases of an exploration program can include the acquisition of seafloor piston cores in an area of interest. Positive results (for example, hydrocarbon presence in the piston cores) showing the presence of a working petroleum system can be valuable in reducing the risks associated with a frontier basin, and also directing exploration efforts to specific zones of interest. Unfortunately, samples leading to positive results in conventional piston core grid sampling campaigns may typically encompass less than 10% of all samples collected. Commonly, piston core grid sampling campaigns involve collecting hundreds of piston core samples, which can be a costly and time consuming effort.

The techniques described in this specification can improve the percentage of positive piston core sampling using techniques to select areas with the highest chances, relative to other areas of the zone of interest, of positive hydrocarbon detection in piston core samples. In some implementations, the techniques described in this specification include one or more of the following: (1) generating a interpretation for the seafloor horizon surface (for example, a map of the seafloor surface) using collected seismic data; (2) performing dip extraction of the seafloor horizon surface to detect one or more locations of potential discontinuities of the seafloor; (3) generating a mirror seafloor surface at the depth of a few hundred feet (for example, 300 feet (ft)); (4) generating a horizon probe using the seafloor horizon surface and the mirror seafloor horizon surface; (5) performing a coherence attribute analysis of the seafloor using the horizon probe (sometimes referred to as variance in this specification) to identify one or more locations of potential discontinuities of the seafloor (which can be added to the locations detected from the dip extraction); (6) performing a curvature seismic attribute analysis and detecting one or more locations of potential discontinuities of the seafloor (which can be added to the locations detected by the dip extraction, the coherence attribute analysis, or both); (7) performing an RMS amplitude realization using the seismic volume between the two seismic horizons (or the volume between the seafloor horizon surface and a distance below the seafloor horizon surface) to detect one or more potential locations of hydrocarbon presence; (8) performing a sweetness seismic attribute analysis to detect one or more potential locations of hydrocarbon presence; (9) selecting areas for sampling from the discontinuities map focusing on the locations with the highest number of discontinuities from the different extraction methods (for example, based on a correlation between the discontinuity locations and the potential locations of hydrocarbon presence).

Figure 1:
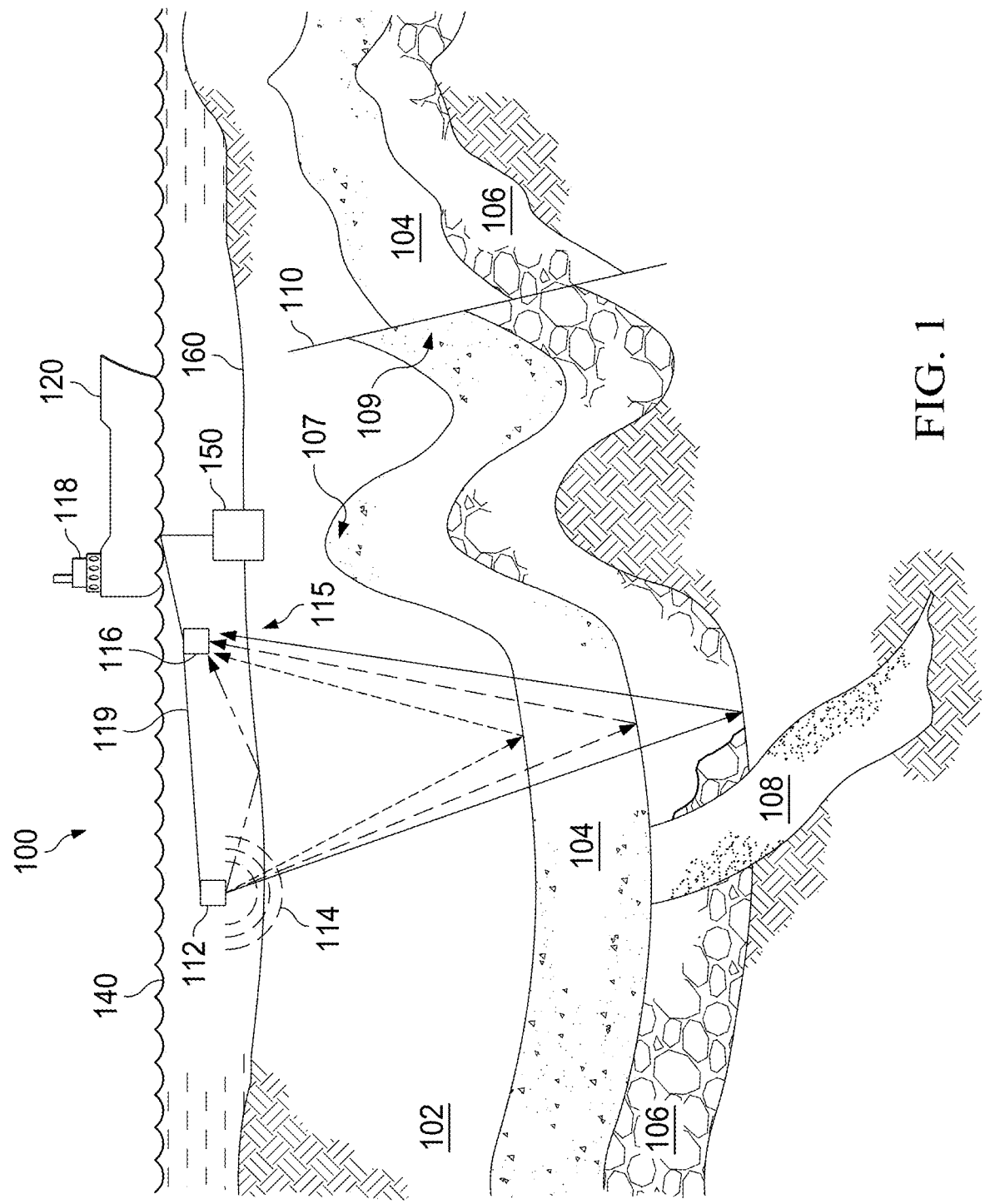
FIG. 1 is a schematic view of a seismic survey being performed to map features such as facies and faults.

FIG. 1 is a schematic view of a seismic survey being performed to map features such as facies and faults in a subsea formation 100. Such seismic surveys can be computationally and resource intensive, and the systems and method described in this specification can facilitate decisions as to whether and where to perform geochemical and piston core sampling. The subterranean formation 100 includes a layer of impermeable cap rock 102 at the surface. Facies underlying the impermeable cap rocks 102 include a sandstone layer 104, a limestone layer 106, and a sand layer 108. A fault line 110 extends across the sandstone layer 104 and the limestone layer 106.

Oil and gas tend to rise through permeable reservoir rock until further upward migration is blocked, for example, by the layer of impermeable cap rock 102. Seismic surveys attempt to identify locations where interaction between layers of the subterranean formation 100 are likely to trap oil and gas by limiting this upward migration. For example, FIG. 1 shows an anticline trap 107, where the layer of impermeable cap rock 102 has an upward convex configuration, and a fault trap 109, where the fault line 110 might allow oil and gas to flow in with clay material between the walls traps the petroleum. Other traps include salt domes and stratigraphic traps.

A seismic source 112 (for example, a seismic airgun) generates seismic waves that propagate through water and into the formation 100. Although illustrated as a single component in FIG. 1, the source or sources 112 are typically a line or an array of sources 112. The generated seismic waves include seismic body waves 114 that travel into the ground and seismic surface waves 115 travel along the ground surface and diminish as they get further from the surface.

The velocity of these seismic waves depends properties, for example, density, porosity, and fluid content of the medium through which the seismic waves are traveling. Different geologic bodies or layers in the formation 100 are distinguishable because the layers have different properties and, thus, different characteristic seismic velocities. For example, in the formation 100, the velocity of seismic waves traveling through the formation 100 will be different in the sandstone layer 104, the limestone layer 106, and the sand layer 108. As the seismic body waves 114 contact interfaces between geologic bodies or layers that have different velocities, each interface reflects some of the energy of the seismic wave and refracts some of the energy of the seismic wave. Such interfaces are sometimes referred to as horizons.

The seismic body waves 114 are received by a sensor or sensors 116. Although illustrated as a single component in FIG. 1, the sensor or sensors 116 are typically a line or an array of sensors 116 that generate an output signal in response to received seismic waves including waves reflected by the horizons in the formation 100 and through the water. The sensors 116 can be hydrophone-receivers that produce electrical output signals transmitted as input data, for example, to computer systems 118 on a vessel 120 floating on a water surface 140 (for example, a boat). Based on the input data, the computer 118 may generate a seismic data output, for example, a seismic two-way response time plot. The sources 112 and the sensors 116 can be coupled to a cable 119 that is suspended beneath or on the water surface 140 and attached to the vessel 120.

In some implementations, results generated by the computer systems 118 may be displayed for user viewing using local or remote monitors or other display units. The computer systems 118 (or some other remote computer systems) can analyze the seismic data received from the sensors 116 and determine one or more locations on the seafloor surface 160 to collect piston core samples using one or more of the techniques described in this specification. The vessel 120 (or some other vessel) can use a piston corer 150 to collect the core samples at the determined one or more locations on the seafloor surface 160.

Figure 2:
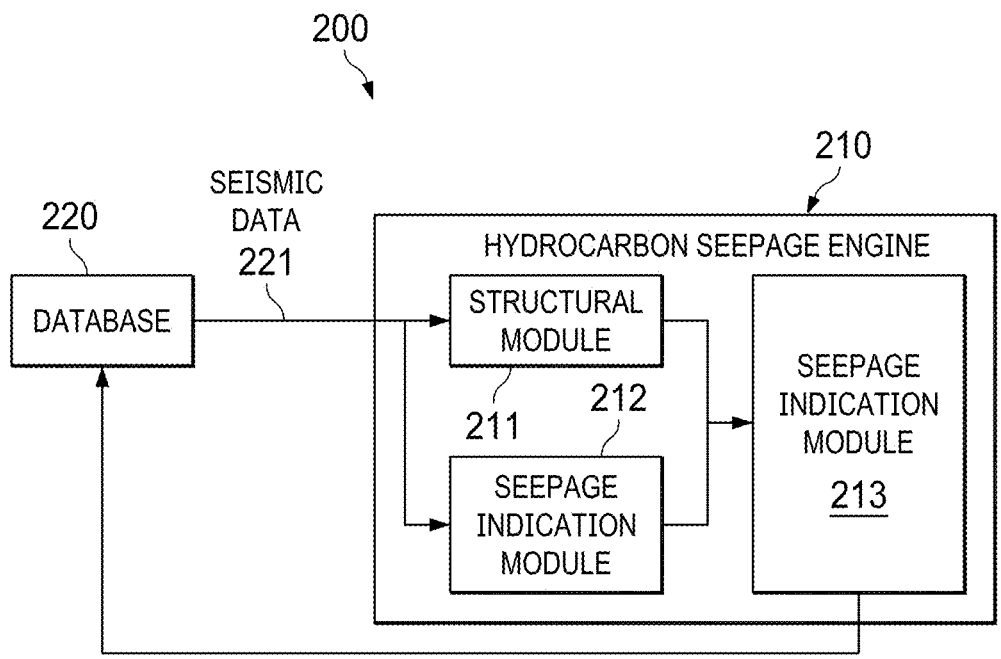
FIG. 2 is a block diagram illustrating an example system for selecting geochemical sample grid locations.

FIG. 2 is a block diagram illustrating an example system 200 for selecting geochemical sample grid locations. The system 200 includes a hydrocarbon seepage engine 210 and a database 220.

The database 220 is configured to store seismic data 221, such as the data received by the hydrophones 116 discussed previously with reference to FIG. 1. The database is communicatively coupled to the hydrocarbon seepage engine 210. In the illustrated implementation, the database 220 is located locally relative to the seepage engine 210 (for example, integrated with the seepage engine 210 or share the same confines as the seepage engine 210). However, in some implementations, the database 220 is located remotely relative to the seepage engine (for example, the database 220 can be integrated with a cloud computing environment).

The seepage engine 210 can include can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the seepage engine 210 includes code-segment having executable instructions.

In some implementations, the seepage engine 210 includes processing mechanisms such as, for example, a general purpose processor, a central processing unit (CPU, at least one application specific integrated circuit (ASIC), general purpose programmable microprocessors, graphic processing units, special-purpose programmable microprocessors, digital signal processors (DSPs), programmable logic arrays (PLAs), field programmable gate arrays (FPGA), special purpose electronic circuits, among others, or a combination of them.

The seepage engine 210 is configured to receive the seismic data 221. The seismic data 221 can be received through any of various techniques, such as wireless communications with the database 220, optical fiber communications, USB, CD-ROM. In some implementations, the seepage engine 210 receivs the seismic data 221 directly from one or more sensors, such as the hydrophones 116 described previously with reference to FIG. 1.

The seepage engine 210 includes a structural module 211, a seepage indication module 212, and a location evaluation module 213. The structural module 211 is configured to generate an interpretation for a seafloor horizon surface using the seismic data 221. The structural module 211 can apply one or more seismic data processing and imaging techniques to the seismic data 221, such as seismic reflection velocity analysis, the generate an image representing an interpretation of the seafloor horizon surface. The interpretation of the seafloor horizon surface can include, for example, a map of the seafloor horizon surface (see, for example, FIG. 5).

Figure 5:
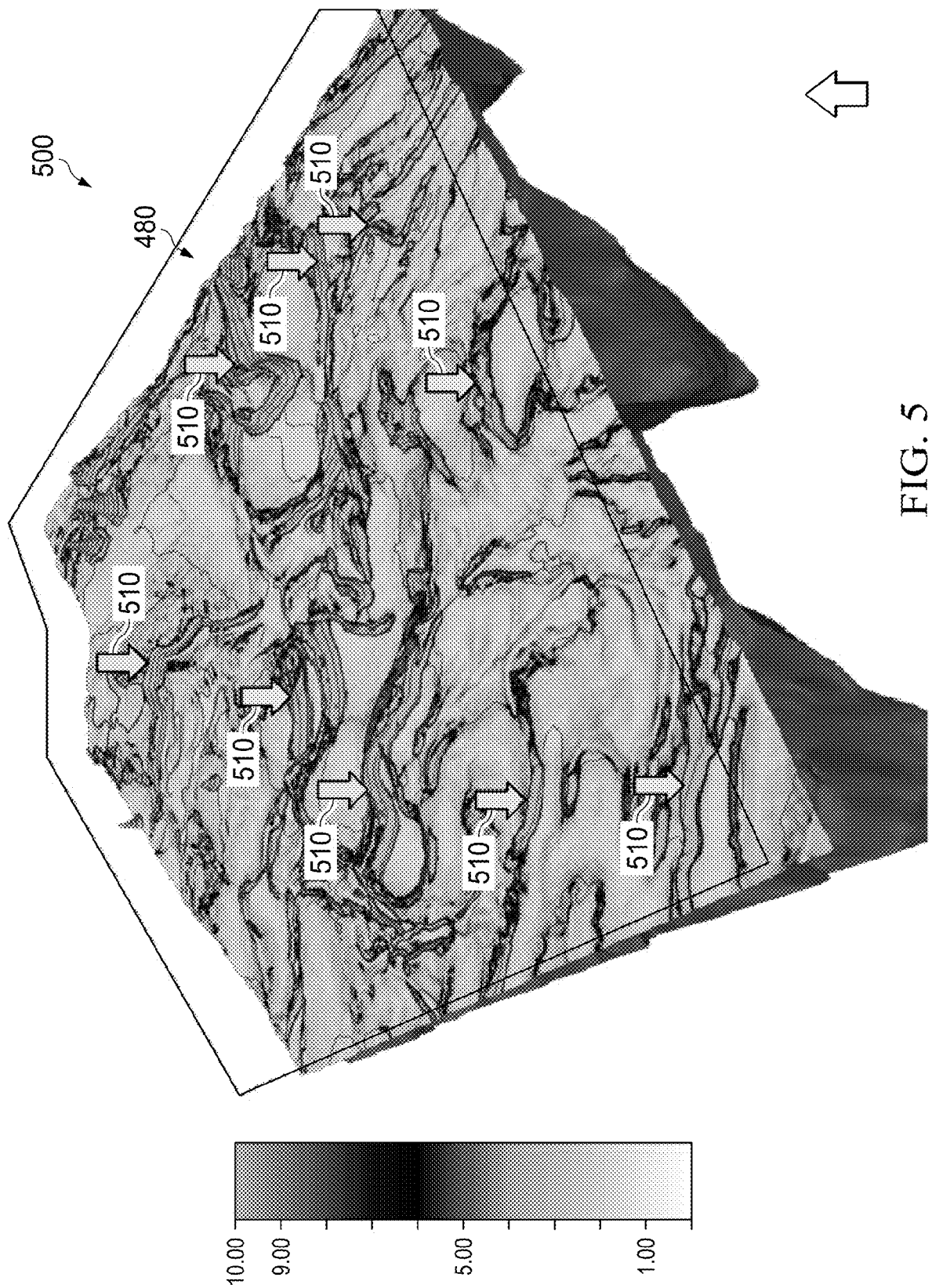
FIG. 5 is an example image representing an interpretation of the seafloor horizon surface.

The structural module 211 is configured to perform a dip extraction analysis of the seafloor horizon surface using the generated image and interpreting discontinuities on the dip extraction (see, for example, FIG. 5). Generally, dip can be defined as the magnitude of the gradient vector calculated at each grid point of the interpreted seafloor horizon surface. The dip extraction analysis can detect locations of possible presence of faults in the seafloor and allow for the detection of zones of the seafloor with the highest dip changes in the surface. That is, the dip extraction analysis can identify locations on the seafloor indicating the potential presence of structural discontinuities (for example, faults) in the surface.

Figure 4:
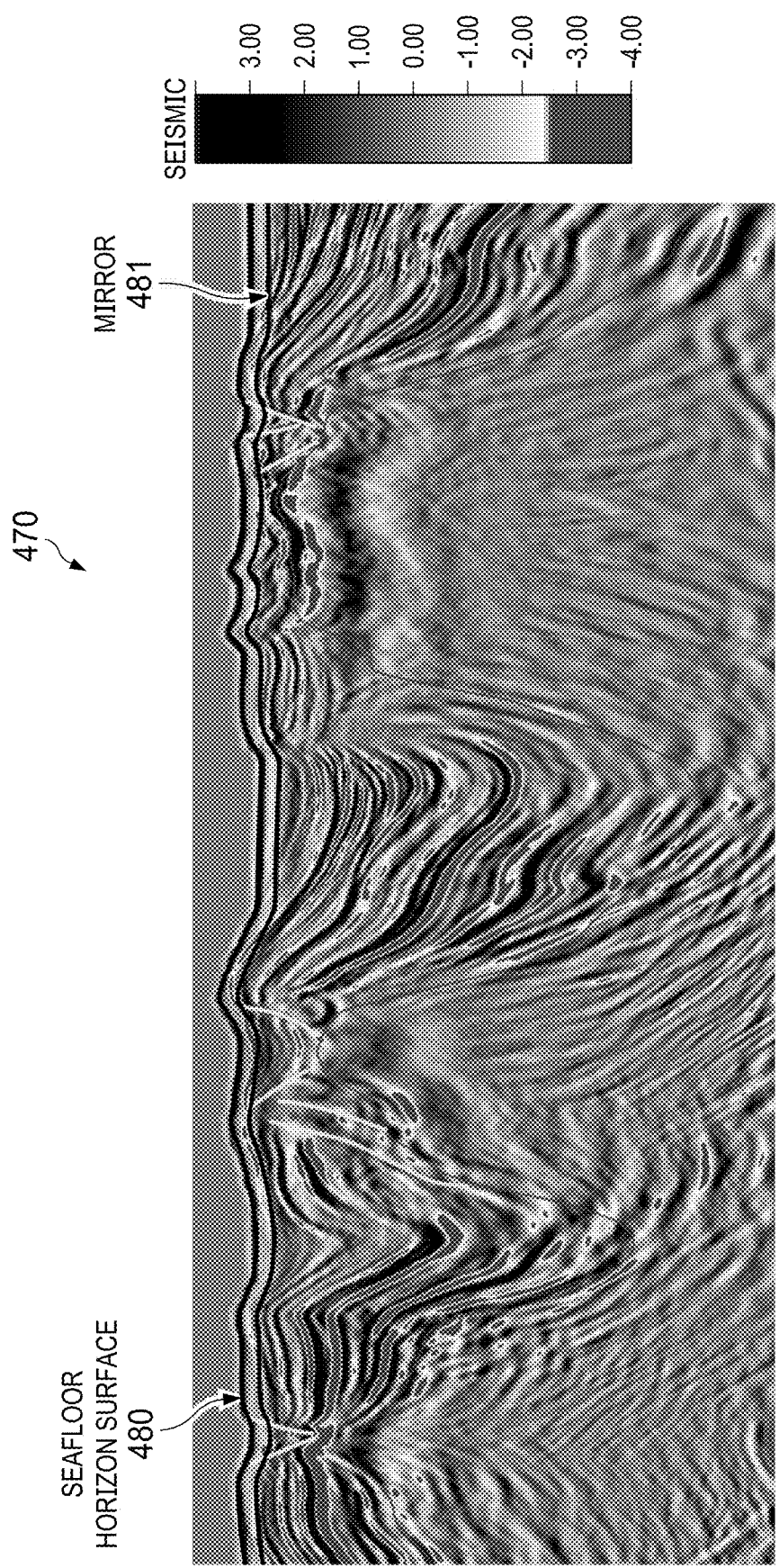
FIG. 4 is an example image illustrating a seafloor horizon surface.

The structural module 211 is configured to generate a mirror seafloor surface at a predetermined depth (for example, 300 feet (ft)) for a seismic attribute window extraction (see, for example, FIG. 4). Although values for the predetermined depth other than 300 ft can be used, in some implementations, 300 ft can be considered an adequate subsurface sampling interval for seismic attribute extraction) and not too distant from the seafloor (for example, the target for the piston core acquisition).

The structural module 211 is configured to generate a seafloor horizon probe using the seafloor horizon surface 480 and the mirror seafloor surface 481. The probe can generally include a constrained seismic volume between the surfaces 480, 481. The structural module 211 is configured to perform a curvature attribute analysis on the probe created between the seafloor horizon surface 480 and the mirror seafloor surface 481 (see, for example, FIG. 6). This can facilitate, for example, further highlighting locations of structural discontinuities not clearly identified by the dip extraction analysis. The curvature attribute analysis can identify, for example, locations of subtle faults, folds, incised channels, differential compaction, and a wide range of other stratigraphic features of the seafloor probe, among others. Generally, curvature can be defined as the 3D property of a quadratic surface that quantifies the degree to which the surfaces deviates from being planar and can measure paleo-deformation. The results of the curvature attribute analysis can be merged with the results from the dip extraction analysis (using, for example, a 90% transparence).

Figure 7:
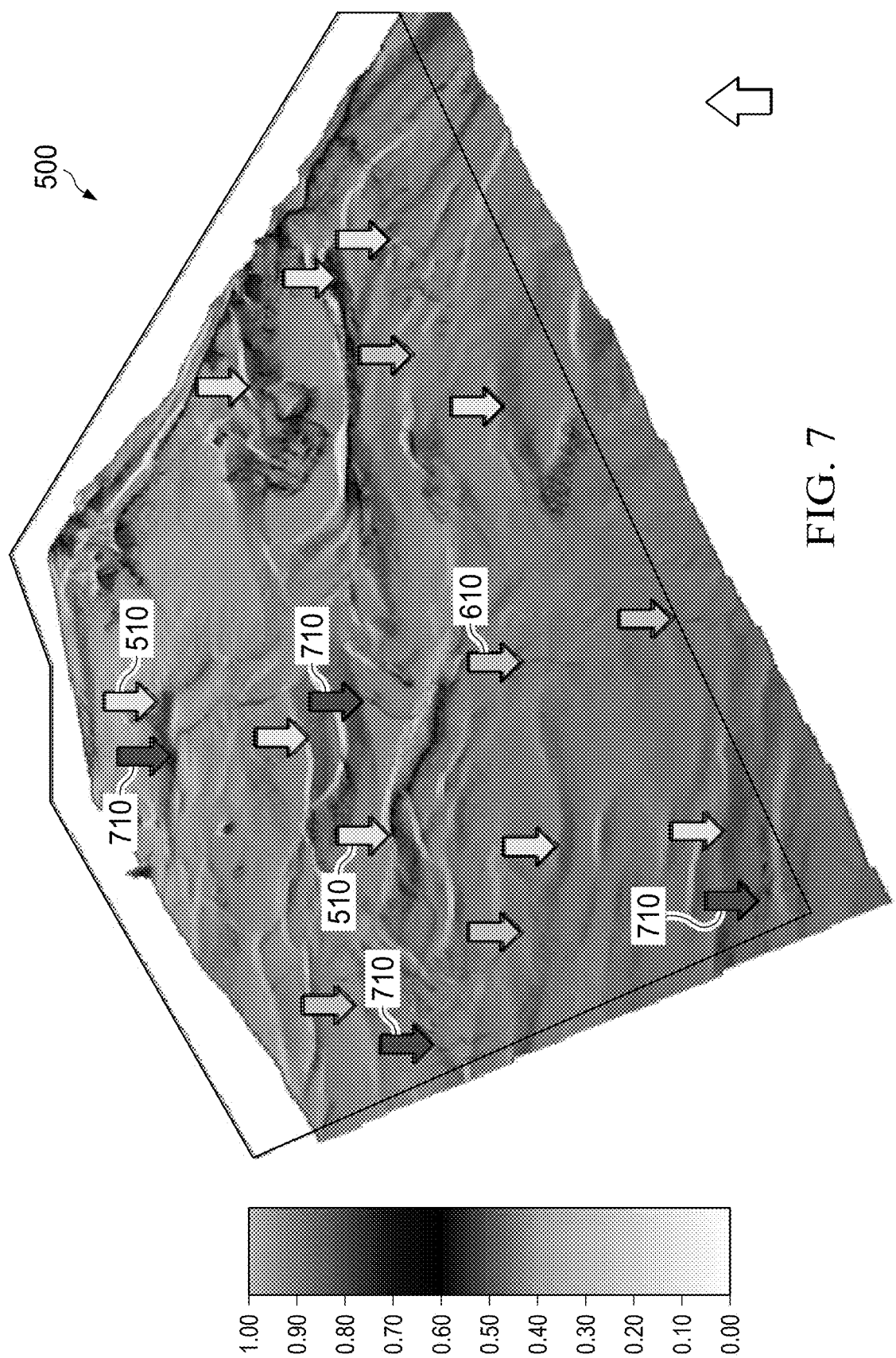
FIG. 7 is the example image of FIGS. 5-6 further illustrating the results of a variance seismic attribute analysis at seafloor level.

The structural module 211 is configured to perform a coherence (variance) attribute analysis of the seafloor using the horizon probe and adding discontinuities identified by the coherence extraction to the previously identified discontinuities from the dip and curvature attribute analysis (see, for example, FIG. 7). This can further highlight locations of potential discontinuities on a subsurface just below the seafloor not captured by the previous curvature and dip analysis. A coherence attribute can generally measure coherence coefficients from seismic amplitude on adjacent traces using, for example, a cross-correlation technique, among others. Generally, coherence can measure the signal similarities of waveform from traces by traces.

The seepage indication module 212 is configured to extract seismic amplitude anomalies (such as RMS amplitude attribute and sweetness attribute) for use as indicators of possible hydrocarbon presence. For example, RMS amplitude and sweetness attributes can be extracted in an interval window (which can have the same thickness as the horizon probe) and the resulting anomalies can then be correlated with topographic features (both positive and negative) and discontinuities on the seafloor (for example, mud mounds, possible fault traces, carbonate build-ups, and so on).

Figure 8:
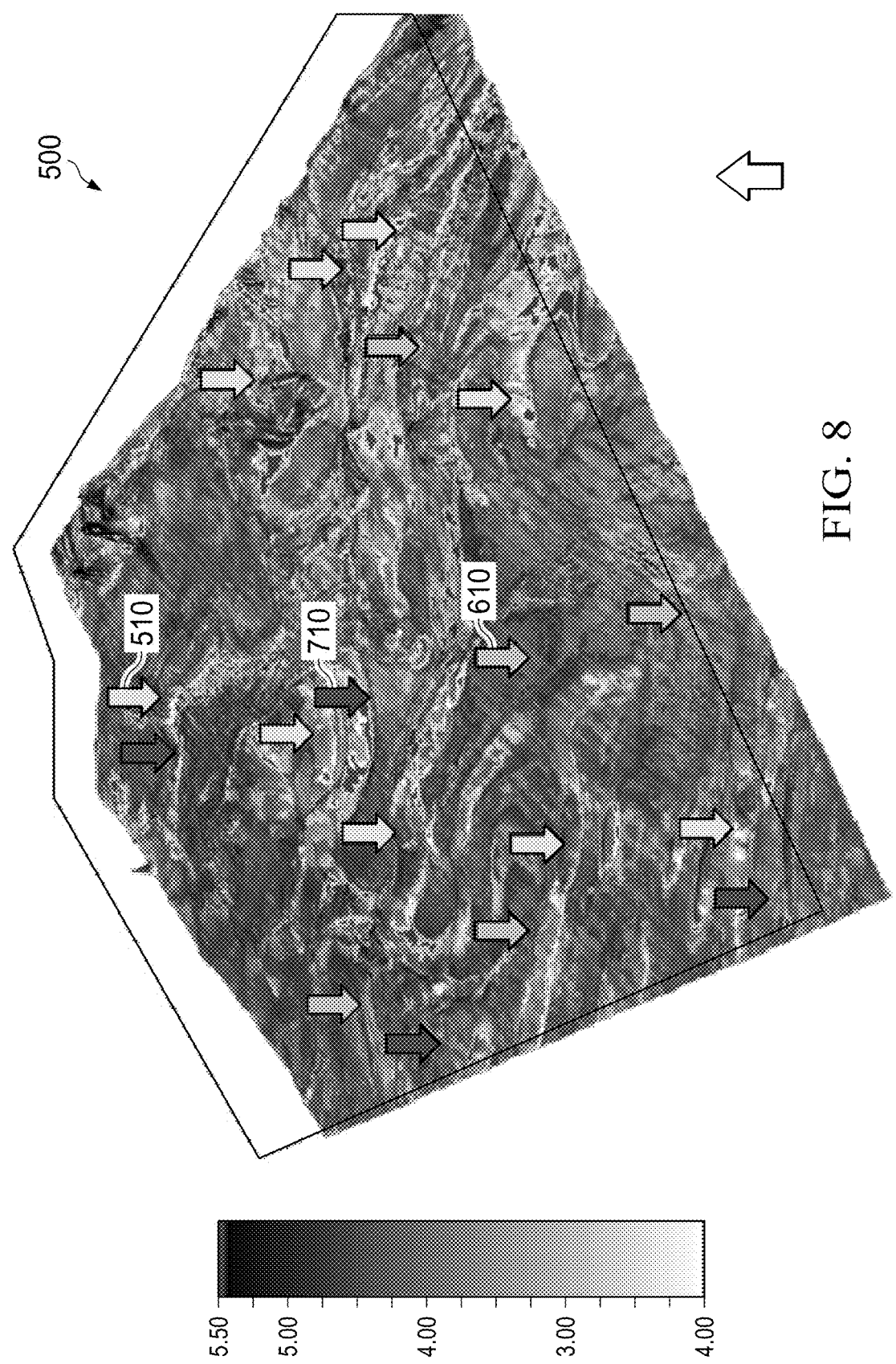
FIG. 8 is the example image of FIGS. 5-7 further illustrating the results of a root mean square (RMS) amplitude analysis of a seismic volume below a seafloor surface.

In some implementations, the seepage indication module 212 is configured to perform an RMS amplitude realization analysis using, for example, at least a portion of the seismic volume between the seafloor horizon surface 480 and the mirror seafloor surface 481, interpret an RMS amplitude map to identify locations of potential amplitude anomalies, and add the results to the seafloor horizon probe (see, for example, FIG. 8). RMS can generally define a post-stack attribute that determines the square root of the sum of squared amplitudes divided by the number of samples within a specified window (for example, a seismic volume between the seafloor horizon surface 480 and the mirror seafloor surface 481). With this root mean square amplitude, one can measure reflectivity in order to map direct hydrocarbon indicators in a zone of interest. For example, extracted RMS amplitude attributes on a selected interval window (for example, a 300 ft interval window below the seafloor horizon surface 480) can show amplitude areas which correspond to zones of bathymetric change. These areas can be a further indication of structural features such as fault traces on the seafloor horizon surface.

Figure 9:
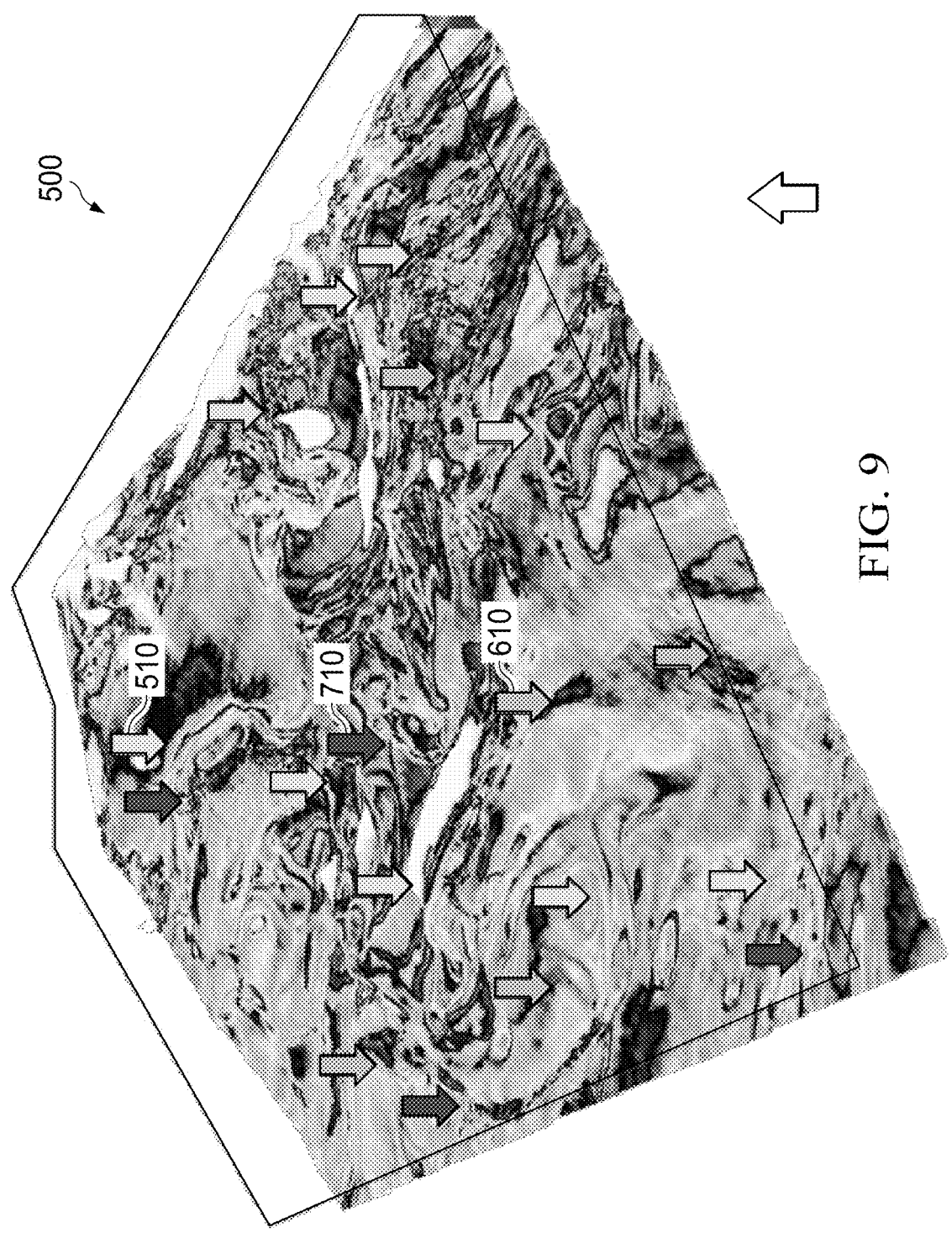
FIG. 9 is the example image of FIGS. 5-8 further illustrating the results of a sweetness seismic attribute analysis of a seafloor horizon surface.
Figure 9:
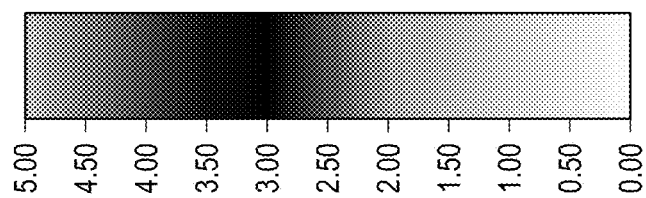

The seepage indication module 212 is configured to perform a sweetness seismic attribute analysis to identify one more locations of sweetness that indicate potential amplitude anomalies, and adding the results to the discontinuities map (see, for example, FIG. 9). Sweetness can be defined as a composite seismic attribute used to highlight thick, clean reservoirs, along with hydrocarbons contained within. Sweetness can be calculated by dividing the instantaneous amplitude (amplitude envelope) by the square root of the instantaneous frequency. Using the mirror seafloor surface 481 (or some distance below the seafloor horizon surface 480), sweetness values can be extracted throughout the seafloor surface. In FIG. 9, sweetness values ranging from 2.00-5.00 are illustrated.

The location evaluation module 213 is configured to select areas for core sampling from the discontinuities map by focusing on the locations with the highest number of discontinuities from the various extraction techniques described previously (for example, curvature attribute analysis, dip extraction analysis, and so forth). In some implementations, the location evaluation module 213 correlates the output from the structural module 211 with the output from the seepage indication module 212 to select the areas for core sampling (see, for example, FIG. 10).

In some implementations, the seepage engine 210 includes control means (for example, control circuitry) for controlling a piston corer (such as the corer 150 described previously with reference to FIG. 1) to lower the corer to the one or more selected locations to obtain a core sample at the one or more locations.

Figure 3:
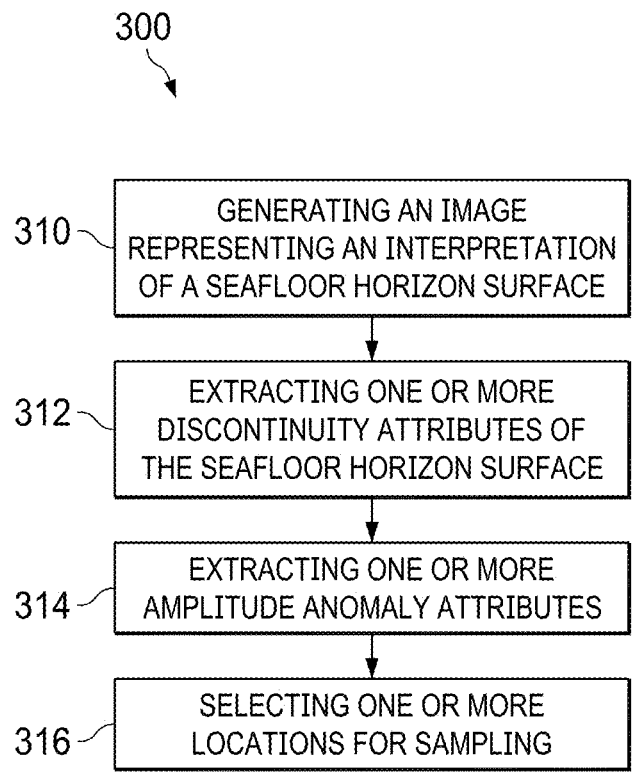
FIG. 3 is flowchart illustrating an example method for selecting geochemical sample grid locations.

FIG. 3 is flowchart illustrating an example method 300 for selecting geochemical sample grid locations. In some implementations, the system 200 discussed previously with reference to FIG. 2 performs all or portions of the method 300. The method 300 includes generating an image representing an interpretation of a seafloor horizon surface (block 310), extracting one or more discontinuity attributes of the seafloor horizon surface (block 312), extracting one or more amplitude attributes (block 314), and selecting one or more locations for sampling (block 316).

A block 310 an image representing an interpretation of a seafloor horizon surface is generated using received seismic date (for example, 3D seismic date received from a sensor, such as a hydrophone). In some implementations, the image interpretation includes a map of the seafloor.

FIG. 4 is an example image 470 illustrating a seafloor horizon surface 480. As illustrated, the example image 470, which was generated using the seismic data 221, shows a cross-section view of the seafloor in which the various layers of the seafloor can be seen. The uppermost layer of the seafloor is identified as the seafloor horizon surface 480. In FIG. 4, amplitude values from 3.00-(−)4.00 are shown.

FIG. 5 is an example image 500 representing an interpretation of the seafloor horizon surface 480.

Referring back to FIG. 3, at block 312 the image and seismic data are used to extract one or more discontinuity attributes of the seafloor horizon surface. In some implementations, block 312 includes performing a dip extraction analysis of the seafloor horizon surface to detect one or more discontinuity locations (for example, dip zone changes) that indicate potential locations of discontinuities of the seafloor horizon surface.

Referring back to FIG. 5, several locations of dip changes 510 that indicate potential discontinuities of the seafloor are noted, and the amount of dip at those locations are interpreted. In FIG. 5, degrees of dip ranging between 1.00-10.00 are shown.

Referring back to FIG. 3, in some implementations, block 312 includes generating a mirror seafloor surface at a predetermined distance below the seafloor horizon surface.

Referring back to FIG. 4, the image 470 illustrates the generated mirror seafloor surface 481, which is located at a depth of approximately 300 ft below the seafloor horizon surface 480.

Referring back to FIG. 3, in some implementations, block 312 includes generating a horizon probe using the seafloor horizon surface and the mirror seafloor surface. In some implementations, block 312 includes performing a curvature attribute analysis of the seafloor horizon surface using the horizon probe to detect one or more discontinuity locations that indicate potential discontinuities of the seafloor horizon surface.

Figure 6:
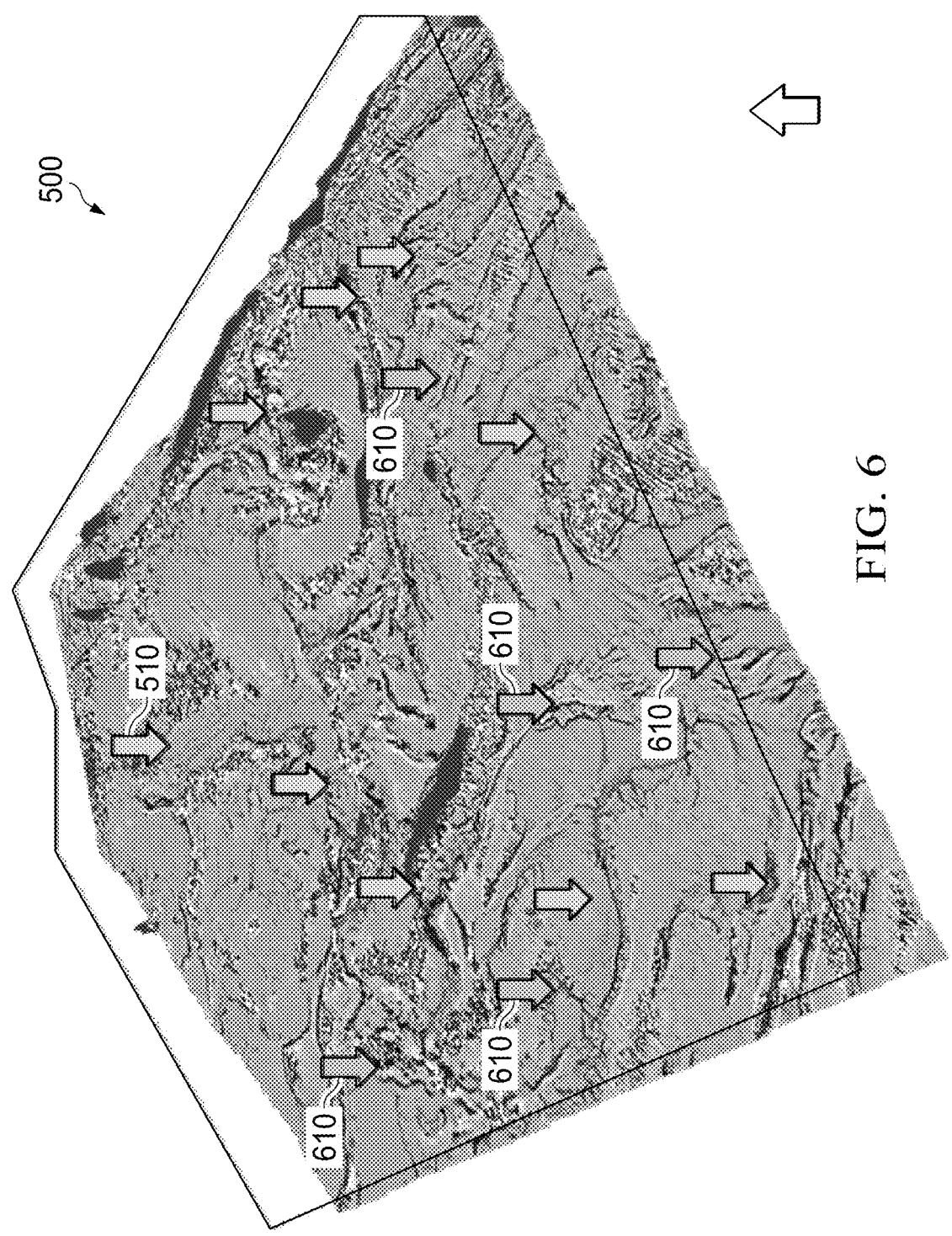
FIG. 6 is the example image of FIG. 5 further illustrating the results of a curvature seismic attribute analysis at seafloor level.
Figure 6:
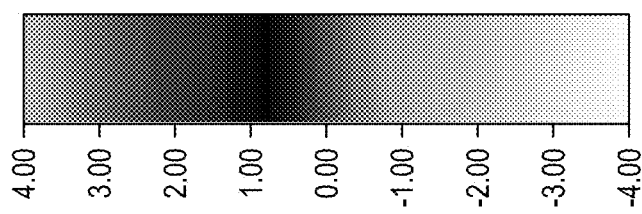

FIG. 6 is the example image 500 of FIG. 5 further illustrating the results of a curvature seismic attribute analysis using a horizon probe at seafloor level. As illustrated, in addition to the dip locations 510 previously identified, locations of curvature 610 that correspond to potential discontinuities of the seafloor are identified as a result of the curvature seismic attribute analysis are added to the horizon probe. The locations of curvature 610 are noted along with the dip locations 510. As will be described in this specification, the image 500 can represent a map of discontinuities along the seafloor horizon surface. In FIG. 6, curvature values ranging from (−)4.00-4.00 are shown. In some implementations, anticlinal features have positive curvature values, synclinal feathers have negative curvature values, and planar features have zero curvature.

Referring back to FIG. 3, in some implementations, block 312 includes performing a variance attribute analysis of the seafloor horizon surface using the horizon probe to detect one or more discontinuity locations that indicate potential discontinuities of the seafloor horizon surface. In some implementations, the mirror seafloor surface is located 300 ft below the seafloor horizon surface.

FIG. 7 is the example image 500 of FIGS. 5-6 further illustrating the results of a coherence (variance) seismic attribute analysis at seafloor level. As shown, one or more locations of variance 710 indicating potential discontinuities are noted, along with the locations 510, 610 identified previously. In FIG. 7, coherence values ranging from 0.00-1.00 are shown. In the illustrated implementation, similar traces are mapped with high coherence coefficients and discontinuities have low coherence coefficients (for example, regions for seismic traces cut by faults).

Referring back to FIG. 3, at block 314, one or more amplitude attributes are extracted using the image and the seismic data. In some implementations, a window extending below the seafloor horizon surface is used to extract the one or more amplitude attributes. In some implementations, block 314 includes performing an RMS amplitude attribute analysis of the seafloor horizon surface using a seismic volume between the seafloor horizon surface and a predetermined distance below the seafloor horizon surface to detect one or more first amplitude anomaly locations that indicate one or more locations of potential amplitude anomalies of the seafloor horizon surface. In some implementations, the seismic volume includes at least a portion of the horizon probe generated in some implementations of block 312.

FIG. 8 is the example image 500 of FIGS. 5-7 further illustrating the results of a root mean square (RMS) amplitude analysis of a seismic volume. As illustrated, the map of the seafloor has been modified to show extracted RMS amplitudes throughout the seafloor, and areas of high RMS amplitude can be seen.

Referring back to FIG. 3, in some implementations, block 314 includes extracting performing a sweetness seismic attribute analysis using the predetermined distance to detect one or more second amplitude anomaly locations that indicate one or more locations of potential amplitude anomalies of the seafloor horizon surface.

FIG. 9 is the example image of FIGS. 5-8 further illustrating the results of a Sweetness seismic attribute analysis of the seafloor horizon surface 480. As shown, a high percentage of the discontinuities observed on the variance and curvature attributes can also be identified through the amplitude anomalies extraction.

Referring back to FIG. 3, at block 316, one or more locations of the seafloor horizon surface is selected for geochemical core sampling based on the one or more discontinuity attributes and the one or more amplitude attributes. In some implementations, block 316 includes determining a correlation between the one or more discontinuity attributes and the one or more amplitude attributes, as described previously in this specification.

Figure 10:
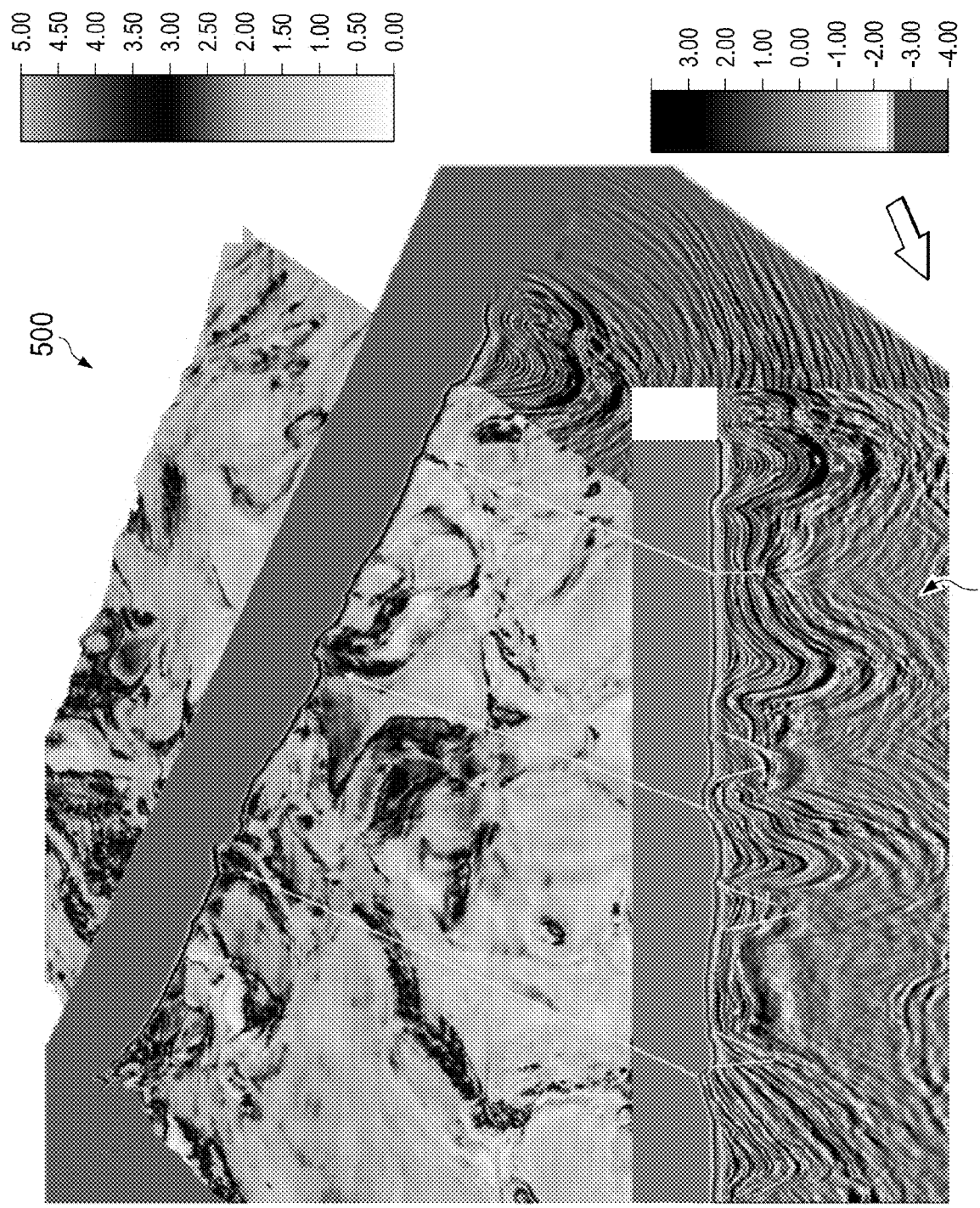
FIG. 10 illustrates correlations between the example image of FIG. 4 and the example image of FIGS. 5-8 highlighting relationships between sweetness attribute and seismic sections.

FIG. 10 illustrates correlations between the example image 470 of FIG. 4 and the example image 500 of FIGS. 5-8 highlighting relationships between Sweetness attribute and seismic sections. Amplitude anomalies, especially when their location coincides with dip, curvature and variance discontinuities, can be interpreted as strong indicators of macro-seepage as many of them are directly related to structural discontinuities such as fault traces.

In some implementations, the method 300 includes using a piston corer to extract a geochemical core sample from the seafloor horizon surface.

While the technology is described in the context of sea exploration, the described technology can be used with land (onshore) seismic data as well.

Figure 11:
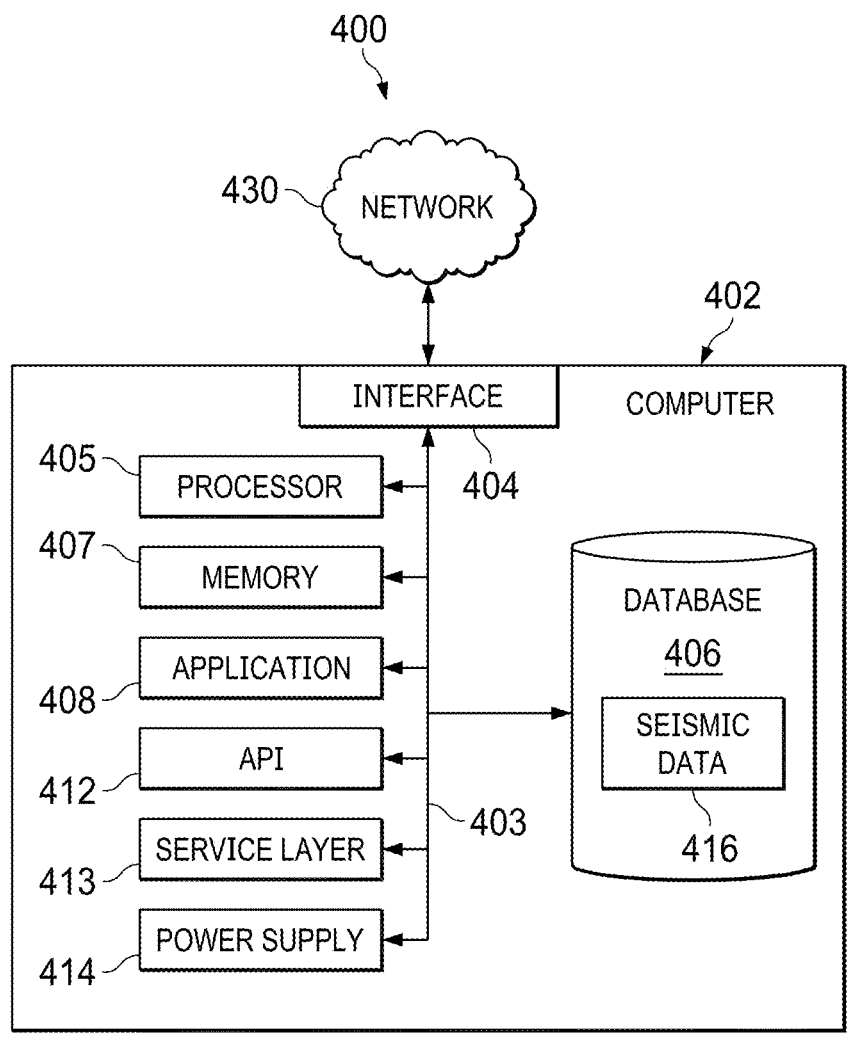
FIG. 11 is a block diagram illustrating an example computer system used to provide computational functionalities associated with described algorithms, methods, functions, processes, flows, and procedures as described in the present disclosure, according to some implementations of the present disclosure.

FIG. 11 is a block diagram of an example computer system 400 used to provide computational functionalities associated with described algorithms, methods, functions, processes, flows, and procedures described in the present disclosure, according to some implementations of the present disclosure. The illustrated computer 402 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 402 can include input devices such as keypads, keyboards, and touch screens that can accept user information. Also, the computer 402 can include output devices that can convey information associated with the operation of the computer 402. The information can include digital data, visual data, audio information, or a combination of information. The information can be presented in a graphical user interface (UI) (or GUI).

The computer 402 can serve in a role as a client, a network component, a server, a database, a persistency, or components of a computer system for performing the subject matter described in the present disclosure. The illustrated computer 402 is communicably coupled with a network 430. In some implementations, one or more components of the computer 402 can be configured to operate within different environments, including cloud-computing-based environments, local environments, global environments, and combinations of environments.

At a high level, the computer 402 is an electronic computing device operable to receive, transmit, process, store, and manage data and information associated with the described subject matter. According to some implementations, the computer 402 can also include, or be communicably coupled with, an application server, an email server, a web server, a caching server, a streaming data server, or a combination of servers.

The computer 402 can receive requests over network 430 from a client application (for example, executing on another computer 402). The computer 402 can respond to the received requests by processing the received requests using software applications. Requests can also be sent to the computer 402 from internal users (for example, from a command console), external (or third) parties, automated applications, entities, individuals, systems, and computers.

Each of the components of the computer 402 can communicate using a system bus 403. In some implementations, any or all of the components of the computer 402, including hardware or software components, can interface with each other or the interface 404 (or a combination of both), over the system bus 403. Interfaces can use an application programming interface (API) 412, a service layer 413, or a combination of the API 412 and service layer 413. The API 412 can include specifications for routines, data structures, and object classes. The API 412 can be either computer-language independent or dependent. The API 412 can refer to a complete interface, a single function, or a set of APIs.

The service layer 413 can provide software services to the computer 402 and other components (whether illustrated or not) that are communicably coupled to the computer 402. The functionality of the computer 402 can be accessible for all service consumers using this service layer. Software services, such as those provided by the service layer 413, can provide reusable, defined functionalities through a defined interface. For example, the interface can be software written in JAVA, C++, or a language providing data in extensible markup language (XML) format. While illustrated as an integrated component of the computer 402, in alternative implementations, the API 412 or the service layer 413 can be stand-alone components in relation to other components of the computer 402 and other components communicably coupled to the computer 402. Moreover, any or all parts of the API 412 or the service layer 413 can be implemented as child or sub-modules of another software module, enterprise application, or hardware module without departing from the scope of the present disclosure.

The computer 402 includes an interface 404. Although illustrated as a single interface 404 in FIG. 11, two or more interfaces 404 can be used according to particular needs, desires, or particular implementations of the computer 402 and the described functionality. The interface 404 can be used by the computer 402 for communicating with other systems that are connected to the network 430 (whether illustrated or not) in a distributed environment. Generally, the interface 404 can include, or be implemented using, logic encoded in software or hardware (or a combination of software and hardware) operable to communicate with the network 430. More specifically, the interface 404 can include software supporting one or more communication protocols associated with communications. As such, the network 430 or the hardware of the interface can be operable to communicate physical signals within and outside of the illustrated computer 402.

The computer 402 includes a processor 405. Although illustrated as a single processor 405 in FIG. 11, two or more processors 405 can be used according to particular needs, desires, or particular implementations of the computer 402 and the described functionality. Generally, the processor 405 can execute instructions and can manipulate data to perform the operations of the computer 402, including operations using algorithms, methods, functions, processes, flows, and procedures as described in the present disclosure.

The computer 402 also includes a database 406 that can hold data (for example, seismic data 416) for the computer 402 and other components connected to the network 430 (whether illustrated or not). For example, database 406 can be an in-memory, conventional, or a database storing data consistent with the present disclosure. In some implementations, database 406 can be a combination of two or more different database types (for example, hybrid in-memory and conventional databases) according to particular needs, desires, or particular implementations of the computer 402 and the described functionality. Although illustrated as a single database 406 in FIG. 11, two or more databases (of the same, different, or combination of types) can be used according to particular needs, desires, or particular implementations of the computer 402 and the described functionality. While database 406 is illustrated as an internal component of the computer 402, in alternative implementations, database 406 can be external to the computer 402.

The computer 402 also includes a memory 407 that can hold data for the computer 402 or a combination of components connected to the network 430 (whether illustrated or not). Memory 407 can store any data consistent with the present disclosure. In some implementations, memory 407 can be a combination of two or more different types of memory (for example, a combination of semiconductor and magnetic storage) according to particular needs, desires, or particular implementations of the computer 402 and the described functionality. Although illustrated as a single memory 407 in FIG. 11, two or more memories 407 (of the same, different, or combination of types) can be used according to particular needs, desires, or particular implementations of the computer 402 and the described functionality. While memory 407 is illustrated as an internal component of the computer 402, in alternative implementations, memory 407 can be external to the computer 402.

The application 408 can be an algorithmic software engine providing functionality according to particular needs, desires, or particular implementations of the computer 402 and the described functionality. For example, application 408 can serve as one or more components, modules, or applications. Further, although illustrated as a single application 408, the application 408 can be implemented as multiple applications 408 on the computer 402. In addition, although illustrated as internal to the computer 402, in alternative implementations, the application 408 can be external to the computer 402.

The computer 402 can also include a power supply 414. The power supply 414 can include a rechargeable or non-rechargeable battery that can be configured to be either user- or non-user-replaceable. In some implementations, the power supply 414 can include power-conversion and management circuits, including recharging, standby, and power management functionalities. In some implementations, the power-supply 414 can include a power plug to allow the computer 402 to be plugged into a wall socket or a power source to, for example, power the computer 402 or recharge a rechargeable battery.

There can be any number of computers 402 associated with, or external to, a computer system containing computer 402, with each computer 402 communicating over network 430. Further, the terms "client," "user," and other appropriate terminology can be used interchangeably, as appropriate, without departing from the scope of the present disclosure.

Moreover, the present disclosure contemplates that many users can use one computer 402 and one user can use multiple computers 402.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY.

The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of implementations of these systems and methods have been described. Nevertheless, it will be understood that various modifications may be made without departing from the spirit and scope of this disclosure. Accordingly, other implementations are within the scope of the following claims.

What is claimed is:

1. A method for geochemical sampling grid locations on a seafloor, the method comprising:

generating, by a processor, using received seismic data, an image representing an interpretation of a seafloor horizon surface;

extracting, by the processor, from the image and based on the seismic data, one or more discontinuity attributes of the seafloor horizon surface by:
- performing a dip extraction analysis of the seafloor horizon surface,
- generating a mirror seafloor surface at a predetermined distance below the seafloor horizon surface, and
- performing a curvature attribute analysis of the seafloor horizon surface;

extracting, by the processor, from the image and based on the seismic data, one or more amplitude attributes of a window extending below the seafloor horizon surface;

combining, by the processor, the one or more discontinuity attributes and the one or more amplitude attributes;

selecting, by the processor, using the image and based at least partly on the combining, one or more locations of the seafloor horizon surface for sampling; and using a piston corer to extract a geological sample at the selected one or more locations.

2. The method of claim 1, wherein using the piston corer to extract the geological sample at the selected one or more locations comprises extracting, using the piston corer, the geological sample at the selected one or more locations.

3. The method of claim 1, wherein selecting the one or more locations includes correlating one or more potential discontinuity locations of the seafloor horizon surface identified using the one or more discontinuity attributes with one or more potential amplitude anomaly locations identified using the one or more amplitude attributes.

4. The method of claim 1, wherein performing the dip extraction analysis of the seafloor horizon surface comprises determining a gradient vector magnitude at one or more locations of the seafloor horizon surface.

5. The method of claim 1, wherein performing the curvature attribute analysis of the seafloor horizon surface comprises determining a deviation of the seafloor horizon surface.

6. The method of claim 1, wherein extracting one or more amplitude attributes comprises performing an root mean square (RMS) amplitude attribute analysis of the seafloor horizon surface using a seismic volume between the seafloor horizon surface and a predetermined distance below the seafloor horizon surface to detect one or more first amplitude anomaly locations that indicate one or more locations of potential amplitude anomalies of the seafloor horizon surface.

7. The method of claim 6, wherein extracting one or more amplitude attributes further comprises performing a sweetness seismic attribute analysis using the predetermined distance to detect one or more second amplitude anomaly locations that indicate one or more locations of potential amplitude anomalies of the seafloor horizon surface.

8. The method of claim 1, wherein extracting one or more discontinuity attributes comprises:
- performing the dip extraction analysis of the seafloor horizon surface to detect one or more first discontinuity locations that indicate potential discontinuities of the seafloor horizon surface;
- generating a horizon probe using the seafloor horizon surface and the mirror seafloor surface; and
- performing the curvature attribute analysis of the seafloor horizon surface using the horizon probe to detect one or more second discontinuity locations that indicate potential discontinuities of the seafloor horizon surface.

9. The method of claim 8, wherein extracting one or more discontinuity attributes further includes performing a variance attribute analysis of the seafloor horizon surface using the horizon probe to detect one or more third discontinuity locations that indicate potential discontinuities of the seafloor horizon surface.

10. The method of claim 8, wherein the mirror seafloor surface is located 300 feet below the seafloor horizon surface.

11. A non-transitory computer storage medium encoded with computer program instructions that when executed by one or more computers cause the one or more computers to perform operations comprising:

generating, using received seismic data, an image representing an interpretation of a seafloor horizon surface;

extracting, from the image and based on the seismic data, one or more discontinuity attributes of the seafloor horizon surface by:
- performing a dip extraction analysis of the seafloor horizon surface,
- generating a mirror seafloor surface at a predetermined distance below the seafloor horizon surface, and
- performing a curvature attribute analysis of the seafloor horizon surface;

extracting, from the image and based on the seismic data, one or more amplitude attributes of a window extending below the seafloor horizon surface;

combining the one or more discontinuity attributes and the one or more amplitude attributes; and selecting, using the image and based at least partly on the combining, one or more locations of the seafloor horizon surface for sampling.

12. The non-transitory computer storage medium of claim 11, the operations further comprising extracting, using a piston corer, a geological sample at the selected one or more locations.

13. The non-transitory computer storage medium of claim 11, wherein selecting the one or more locations includes correlating one or more potential discontinuity locations of the seafloor horizon surface identified using the one or more discontinuity attributes with one or more potential amplitude anomaly locations identified using the one or more amplitude attributes.

14. The non-transitory computer storage medium of claim 11, wherein extracting one or more amplitude attributes comprises performing an root mean square (RMS) amplitude attribute analysis of the seafloor horizon surface using a seismic volume between the seafloor horizon surface and a predetermined distance below the seafloor horizon surface to detect one or more first amplitude anomaly locations that indicate one or more locations of potential amplitude anomalies of the seafloor horizon surface.

15. The non-transitory computer storage medium of claim 14, wherein extracting one or more amplitude attributes further comprises performing a sweetness seismic attribute analysis using the predetermined distance to detect one or more second amplitude anomaly locations that indicate one or more locations of potential amplitude anomalies of the seafloor horizon surface.

16. The non-transitory computer storage medium of claim 11, wherein extracting one or more discontinuity attributes comprises:

performing the dip extraction analysis of the seafloor horizon surface to detect one or more first discontinuity locations that indicate potential discontinuities of the seafloor horizon surface;

generating a horizon probe using the seafloor horizon surface and the mirror seafloor surface; and performing the curvature attribute analysis of the seafloor horizon surface using the horizon probe to detect one or more second discontinuity locations that indicate potential discontinuities of the seafloor horizon surface.

17. The non-transitory computer storage medium of claim 16, wherein extracting one or more discontinuity attributes further includes performing a variance attribute analysis of the seafloor horizon surface using the horizon probe to detect one or more third discontinuity locations that indicate potential discontinuities of the seafloor horizon surface.

18. The non-transitory computer storage medium of claim 16, wherein the mirror seafloor surface is located 300 feet below the seafloor horizon surface.

19. A system comprising:
a computer-readable medium comprising computer-executable instructions; and
at least one processor configured to execute the computer-executable instructions, wherein when the at least one processor executes the computer-executable instructions the at least one processor is configured to perform operations comprising:
generating, using received seismic data, an image representing an interpretation of a seafloor horizon surface;
extracting, from the image and based on the seismic data, one or more discontinuity attributes of the seafloor horizon surface by:
performing a dip extraction analysis of the seafloor horizon surface,
generating a mirror seafloor surface at a predetermined distance below the seafloor horizon surface, and
performing a curvature attribute analysis of the seafloor horizon surface;
extracting, from the image and based on the seismic data, one or more amplitude attributes of a window extending below the seafloor horizon surface;
combining the one or more discontinuity attributes and the one or more amplitude attributes; and
selecting, using the image and based at least partly on the combining, one or more locations of the seafloor horizon surface for sampling.

20. The system of claim 19, wherein extracting one or more discontinuity attributes comprises:
performing the dip extraction analysis of the seafloor horizon surface to detect one or more first discontinuity locations that indicate potential discontinuities of the seafloor horizon surface;
generating a horizon probe using the seafloor horizon surface and the mirror seafloor surface; and
performing the curvature attribute analysis of the seafloor horizon surface using the horizon probe to detect one or more second discontinuity locations that indicate potential discontinuities of the seafloor horizon surface.

21. The system of claim 20, wherein extracting one or more discontinuity attributes further includes performing a variance attribute analysis of the seafloor horizon surface using the horizon probe to detect one or more third discontinuity locations that indicate potential discontinuities of the seafloor horizon surface.

22. The system of claim 21, wherein extracting one or more amplitude attributes comprises performing an root mean square (RMS) amplitude attribute analysis of the seafloor horizon surface using a seismic volume between the seafloor horizon surface and a predetermined distance below the seafloor horizon surface to detect one or more first amplitude anomaly locations that indicate one or more locations of potential amplitude anomalies of the seafloor horizon surface.

23. A method for geochemical sampling grid locations on a seafloor, the method comprising:
generating, by a processor, using received seismic data, an image representing an interpretation of a seafloor horizon surface;
extracting, by the processor, from the image and based on the seismic data, one or more discontinuity attributes of the seafloor horizon surface by:
performing a dip extraction analysis of the seafloor horizon surface to detect one or more first discontinuity locations that indicate potential discontinuities of the seafloor horizon surface;
generating a mirror seafloor surface at a predetermined distance below the seafloor horizon surface;
generating a horizon probe using the seafloor horizon surface and the mirror seafloor surface; and
performing a curvature attribute analysis of the seafloor horizon surface using the horizon probe to detect one or more second discontinuity locations that indicate potential discontinuities of the seafloor horizon surface;
extracting, by the processor, from the image and based on the seismic data, one or more amplitude attributes of a window extending below the seafloor horizon surface;
combining, by the processor, the one or more discontinuity attributes and the one or more amplitude attributes;
selecting, by the processor, using the image and based at least partly on the combining, one or more locations of the seafloor horizon surface for sampling; and
using a piston corer to extract a geological sample at the selected one or more locations.

\* \* \* \* \*